United States Patent [19]

Mobilio et al.

[11] Patent Number: 4,687,860
[45] Date of Patent: * Aug. 18, 1987

[54] SUBSTITUTED 2,3,4,9-TETRAHYDRO-1H-CARBAZOLE-1-ACETIC ACID

[75] Inventors: Dominick Mobilio; Christopher A. Demerson, both of Plainsboro; Leslie G. Humber, North Brunswick, all of N.J.

[73] Assignee: American Home Products Corporation, New York, N.Y.

[*] Notice: The portion of the term of this patent subsequent to Oct. 7, 2003 has been disclaimed.

[21] Appl. No.: 900,488

[22] Filed: Aug. 26, 1986

Related U.S. Application Data

[60] Continuation-in-part of Ser. No. 830,598, Feb. 18, 1986, which is a division of Ser. No. 797,561, Nov. 13, 1985, Pat. No. 4,616,028, which is a continuation-in-part of Ser. No. 726,197, Apr. 22, 1985, abandoned.

[51] Int. Cl.$^4$ .......................................... C07D 209/82
[52] U.S. Cl. ..................................................... 548/439
[58] Field of Search ........................................ 548/439

[56] References Cited

U.S. PATENT DOCUMENTS 4,616,028 10/1986 Mobilio et al. ..................... 548/439

Primary Examiner—Robert W. Ramsuer
Attorney, Agent, or Firm—Walter Patton

[57] ABSTRACT

Substituted 2,3,4,9-tetrahydro-1H-carbazole-1-acetic acid derivatives and methods for their preparation and use are disclosed. The compounds are useful analgesic and antiinflammatory agents.

4 Claims, No Drawings 4,687,860

SUBSTITUTED 2,3,4,9-TETRAHYDRO-1H-CARBAZOLE-1-ACETIC ACID

This is a continuation-in-part patent application of copending U.S. Ser. No. 830,598, filed Feb. 18, 1986, which in turn is a divisional patent application of copending U.S. Ser. No. 797,561, filed Nov. 13, 1985 now U.S. Pat. No. 4,616,028, which in turn is a continuation-in-part patent application of copending U.S. Ser. No. 726,197, filed Apr. 22, 1985, now abandoned.

BACKGROUND OF THE INVENTION a. Field of Invention

This invention relates to tricyclic acetic acid derivatives, to their preparation and use, and to intermediates used for their preparation.

More specifically, this invention relates to tricyclic acetic acid derivatives in which the tricyclic portion thereof is characterized by having an indole portion fused to a cyclohexane ring. Still more specifically, the compounds of this invention are characterized as derivatives of the following tricyclic acetic acid system:

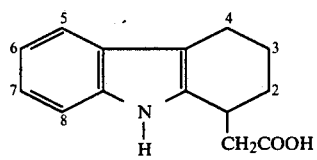

2,3,4,9-tetrahydro-1H-carbazole-1-acetic acid in which the carbons at the 1-, 4-, 7- and 8-positions are further substituted.

The tricyclic acetic acid compounds of this invention possess useful pharmacologic properties; for instance, they exhibit analgesic and antiinflammatory activity at dose levels which do not elicit undesirable side effects. The foregoing combination of attributes renders the compounds of this invention useful for the treatment of inflammatory conditions and of pain.

b. Prior Art

The closest prior art to the present invention is:

Asselin et al. U.S. Pat. No. 4,057,559. Asselin discloses analgesic and antiinflammatory agents having the same heterocyclic ring system as the present invention but without the substituents of the present invention.

Demerson et al. U.S. Pat. No. 3,939,178 discloses 1,3,4,9-tetrahydropyrano[3,4-b]indoles and 1,3,4,9-tetrahydrothiopyrano[3,4-b]indoles having analgesic and antiinflammatory activity. Related U.S. Pats. are Nos. 3,974,179 and 3,843,681.

Boehringer Mannheim European Patent 42593 generically discloses starting materials useful for producing cardiotonic and beta-blocking agents. The starting materials include 1,2,3,4-tetrahydrocarbazoles with substituents selected from the broad group including hydrogen, carboxy, lower alkyl and lower alkenyl. The starting materials are in each case also substituted with a reactive group which distinguishes them from the compounds of the present invention.

Further removed, related patents that include tetrahydrocarbazoleacetic acid derivatives useful as analgesic and anti-inflammatory agents are U.S. Pat. Nos. 4,234,487; 4,264,500; 4,193,923; 4,158,007; 4,146,542; 3,896,145 and 3,824,314; Japanese Pat. No. J51032556; Netherland Pat. No. NL 7,100,213 and Great Britain Pat. No. GB 1385620.

SUMMARY OF THE INVENTION

The compounds of this invention are represented by formula (I)

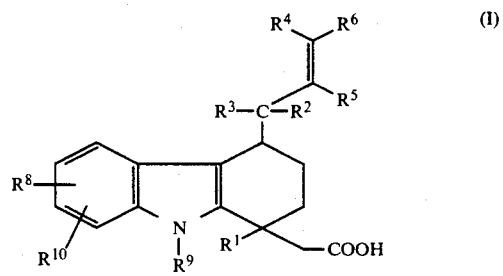

wherein $R^1$, $R^2$, $R^3$, $R^4$, $R^5$ and $R^6$ are hydrogen or lower alkyl or $R^3$ and $R^4$ may be joined together to form $(CH_2)_m$ or $R^5$ and $R^6$ may be joined together to form —CH=CH—CH=CH—, $(CH_2)_n$, —CH=CH—O— or —CH=CH—S—, $R^8$ and $R^{10}$ are independently hydrogen, lower alkyl or halogen, $R^9$ is hydrogen or lower alkyl, m is 2 to 3, and n is 2 to 4 and the pharmaceutically acceptable salts thereof.

A preferred aspect of the present invention are the compounds represented by formula (II).

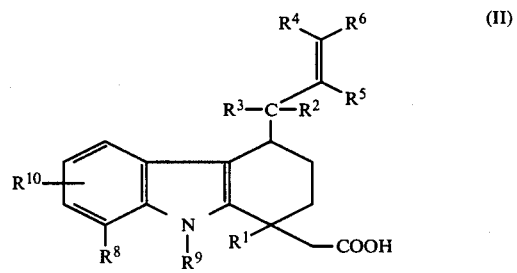

wherein $R^1$, $R^2$, $R^3$, $R^4$, $R^5$, and $R^6$ are independently hydrogen or lower alkyl containing 1 to 6 carbon atoms or $R^3$ and $R^4$ may be joined together to form $(CH_2)_3$ or $R^5$ and $R^6$ may be joined together to form

—CH=CH—CH=CH—, $(CH_2)_4$,

—CH=CH—O— or —CH=CH—S—, $R^8$ and $R^{10}$ are independently hydrogen, lower alkyl containing 1 to 6 carbon atoms or halogen, $R^9$ is hydrogen or lower alkyl containing 1 to 6 carbon atoms, and the pharmaceutically acceptable salts thereof.

A still further preferred aspect of the present invention are the compounds represented by formula (III)

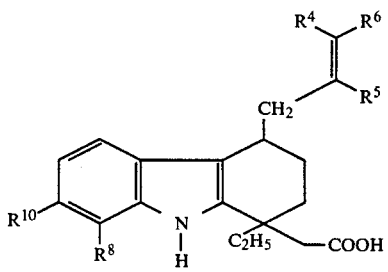 (III)

wherein $R^4$, $R^5$ and $R^6$ are hydrogen or $R^5$ and $R^6$ may be joined together to form —CH=CH—CH=CH—, $R^8$ are $R^{10}$ are independently hydrogen, methyl, ethyl or chlorine and the pharmaceutically acceptable salts thereof.

The most preferred compounds of the present invention are designated cis-1,8-diethyl-2,3,4,9-tetrahydro-4-(2-propenyl)-1H-carbazole-1-acetic acid, cis-1-ethyl-2,3,4,9-tetrahydro-4-(2-propenyl)-1H-carbazole-1-acetic acid, 1,8-diethyl-2,3,4,9-tetrahydro-4-(phenylmethyl)-1H-carbazole-1-acetic acid, cis-7,8-dichloro-1-ethyl-2,3,4,9-tetrahydro-4-(2-propenyl)-1H-carbazole-1-acetic acid, cis-7-chloro-1-ethyl-2,3,4,9-tetrahydro-8-methyl-4-(2-propenyl)-1H-carbazole-1-acetic acid, cis-1-ethyl-2,3,4,9-tetrahydro-8-methyl-4-(2-propenyl)-1H-carbazole-1-acetic acid, cis-1-ethyl-7,8-difluoro-2,3,4,9-tetrahydro-4-(2-propenyl)-1H-carbazole-1-acetic acid and the pharmaceutically acceptable salts thereof.

The compounds of the present invention are prepared by a process in which the unsaturated ketone of structure (IV)

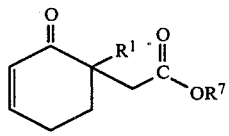 (IV)

wherein $R^1$ is as defined above and $R^7$ is lower alkyl is reacted with organometallic reagent

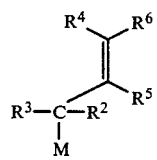

wherein $R^2$, $R^3$, $R^4$, $R^5$ and $R^6$ are as defined above and M maybe $SiMe_3$ as described by H. Sakurai in Pure Apple Chem., 54, 1 (1982), or $SnBu_3$, in both cases carrying out the reaction in the presence of an acid such as titanium tetrachloride, or M may be MgBr, MgCl or MgI, carrying out the reaction in the presence of a suitable copper catalyst selected from the group consisting of copper bromide dimethyl sulfide complex, cuprous iodide, cuprous bromide, copper acetate, cuprous chloride and tributylphosphine cuprous iodide complex, to obtain a compound or compounds of structures Va, Vb, Vc or Vd.

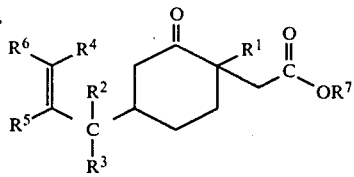 (Va)

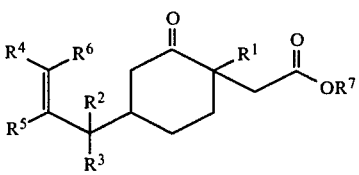 (Vb)

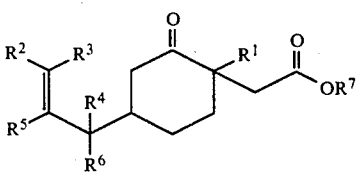 (Vc)

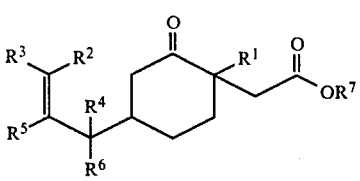 (Vd)

wherein $R^1$, $R^2$, $R^3$, $R^4$, $R^5$ $R^6$ and $R^7$ are as defined above and further reacting a compound of structure (V) with the substituted hydrazine of formula (VI)

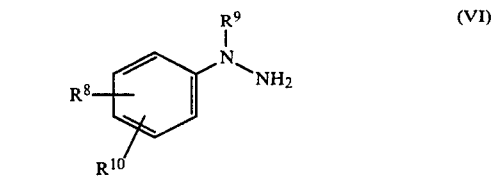 (VI)

wherein $R^8$ and $R^{10}$ are independently hydrogen, lower alkyl or halogen and $R^9$ is hydrogen or lower alkyl to obtain the corresponding hydrazone of structure (VII)

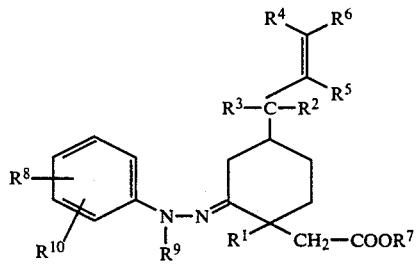 (VII)

wherein $R^1$, $R^2$, $R^3$, $R^4$, $R^5$, $R^6$, $R^7$, $R^8$, $R^9$ and $R_{10}$ are as defined above. The hydrazone is treated with a cyclizing agent to give the ester of compound (I) and after hydrolyzing said ester compound (I) is obtained.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "halogen" as used herein includes fluorine, chlorine, bromine and iodine.

The compounds of formula (I) form salts with suitable pharmaceutically acceptable inorganic and organic bases. These derived salts possess the same activity as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; phenyl substituted alkylamines, such as benzenemethanamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) is dissolved in a suitable solvent of either moderate or low polarity, for example, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention are the diastereo isomers wherein the 4-substituent is either cis or trans to the acetic acid chain at position one.

Also included in this invention are the optical isomers of the compounds of formula (I) which result from asymmetric centers, contained therein. Such isomers are obtained in substantially pure form by classical separation techniques and by sterically controlled synthesis.

ANTIINFLAMMATORY ACTIVITY

The useful antiinflammatory activities of the tricyclic acetic acid derivatives of formula (I) are demonstrated in standard pharmacologic tests, for example, the test designated: PREVENTATIVE ADJUVANT EDEMA The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access water but food is withdrawn 18 hours before testing.

Drug Preparations and Administration:

Freund's complete adjuvant is prepared by suspending 5 mg killed and dried Mycobacterium butyricum (Difco) in 1 mL liquid paraffin. The test compounds are dissolved in distilled water or suspended in distilled water with a few drops of Tween 80 according to their solubility. For primary screening all drugs are administered by gastric lavage at the arbitrary dosage of 100 mg/kg, p.o. in a volume of 0.5 mL/100 g body weight to groups of 10 animals.

Methodological Details:

The method is essentially that described by Wax et al., J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (day 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Phenylbutazone (50 mg/kg, p.o.) is included as a positive control.

Presentation of Results:

The mean edema volume (expressed as mL±SEM) is calculated for each group and the percentage protection conferred by the drug is calculated:

$$\% \text{ protection} = \frac{(c - t) \, 100}{c}$$

where c is the mean edema volume for the untreated controls and t is the mean edema volume for the drug treated group.

A further test used to determine the utility of the compounds of the present invention is designated: DRUG EFFECTS ON PHENYLQUINONE-INDUCED WRITHING IN MICE The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% methyl cellulose or 0.5% Tween 80. They are administered by gastric lavage in a volume of 5 mL/kg. For primary screening all drugs are administered at the arbitrary dosage of 200 mg/kg, p.o. to a group of 10 mice.

Methodological Details:

A modification of the method of Siegmund et al., Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylquinone (PBQ; 2-phenyl-1,4-benzoquinone) and placed in individual observation boxes. The number of writhing or abdominal squirming movements made by each mouse during the following 15 minutes period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t)\,100}{c}$$

where c = mean number of writhes in the control group
where t = mean number of writhes in the test drug group A still further test used to determine the utility of the compounds of the present invention is designated: PAW PRESSURE TEST IN THE RAT The objective of this test is to assess the potency of peripheral and central acting drugs in inhibiting the reaction of rats to painful stimulation applied to an inflamed paw.

Species:

Male Sprague Dawley rats (180–200 g) are used. The animals are fasted overnight prior to drug administration.

Drug Preparation and Administration:

Freund's Complete Adjuvant (FCA) is prepared by suspending 5 mg killed and dried mycobacterium butyricum (Difco) in 1 mL liquid paraffin. The test compounds are dissolved, or suspended with a few drops of Tween 80, in distilled water according to their solubility. They are administered by gastric gavage in a volume of 0.5 mL/100 g body weight to groups of 10 animals.

Methodological Details:

Ten rats are used per group. The method is essentially that described by Randall, et al., Arch. Int. Pharmacodyn. 111, 409 (1957) and the apparatus which is used to apply pressure to the paw (Analgesy-meter for the rat paw, Ugo Basile from Coulbourn Instruments) is a modification of that described by Gilfoil et al., J. Pharmacol. 142, 1 (1963). The instrument is basically a device which exerts a force that increases at a constant rate. The force is continuously monitored by a pointer moving along a linear scale and is measured in grams. The inflammatory reaction is induced in the left hind paw of rats by injecting 0.1 mL of Freund's adjuvant intradermally. The test compound or vehicle is administered 24 hours after the adjuvant. Prior to drug administration the rats are selected for their paw sensitivity. Rats responding to a pain threshold greater than 10 g applied to the inflamed paw are rejected. The pain threshold (vocalization) is determined 1 and 3 hours later in the inflamed paw and the normal paw of the treated and control groups. The higher of the 2 readings will be considered as representative of the drug effect on the pain threshold.

Presentation of results and Criteria for Activity:

Each animal which has a reading 1.5 times greater than the mean reading of the control-group will be considered as responsive to treatment. The number of animals showing an analgesic effect is then determined in each group.

The $ED_{50}$ (dose which causes analgesia in 50% of the animals) using at least 3 doses is then determined, by the method described in Litchfield et al., J. Pharmacol. Exp. Ther., 96, 99 (1949).

Typical results obtained for the compounds of the present invention in the aforementioned tests are as follows:

| Compound | Dose (mg/kg, p.o.) | % Inhibition |
|---|---|---|
| Preventative Adjuvant Edema | | |
| Example 1 | 10 | 31 |
|  | 25 | 44 |
|  | 50 | 38 |
| Example 2 Isomer A | 25 | 6 |
| Example 2 Isomer B | 25 | 38 |
| Example 3 | 10 | 50 |
| Phenylquinone Writhing in Mice | | |
| Example 1 | 10.6 | 31 |
|  | 25 | 60–80 |
|  | 200 | 94 |
| Example 2 Isomer A | 25 | 15 |
| Example 2 Isomer B | 25 | 55 |
| Example 3 | 20 | 50 |
| 4-propyl-1,8-diethyl-2,3,4,9-tetrahydro-1H—carbazole-1-acetic acid U.S. Pat. No. 4,057,559 | 25 | 15 |
|  | 200 | 56 |

| Compound | $ED_{50}$ (mg/kg, p.o.) |
|---|---|
| Paw Pressure Test in the Rat | |
| Example 1 | 0.02 |
| Example 3 | 0.01 |

The lack of side effects for the compounds of this invention are demonstrated by standard acute toxicity tests described by R. A. Turner in "Screening Methods in Pharmacology," Academic Press, New York and London, 1965, pp. 152-163 and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula I of this invention will vary with the particular compound chosen and form of administration. Furthermore, it will vary with the particular host under treatment. Generally, the compounds of this invention are administered at a concentration level that affords protective effects without any deleterious side effects. These anti-inflammatorily and analgesic effective concentration levels are usually obtained within a therapeutic range of 1.0 µg to 500 mg/kg per day, with a preferred range of 10 µg to 100 mg/kg per day.

The compounds of this invention also possess antipyretic activity.

The compounds of this invention may be administered in conjunction with nonsteroid anti-inflammatory drugs such as acetaminophen, ibuprofen and aspirin an/or with opiate analgesics such as codeine, oxycodone and morphine together with the usual doses of caffeine. When used in combination with other drugs, the dosage of the compounds of the present invention is adjusted accordingly.

The preferred process for obtaining the compounds of the present invention is exemplified by the process for obtaining 4-substituted-1,8-diethyl-2,3,4,9-tetrahydro-1H-carbozole-1-acetic acids (XII) outlined in Scheme 1.

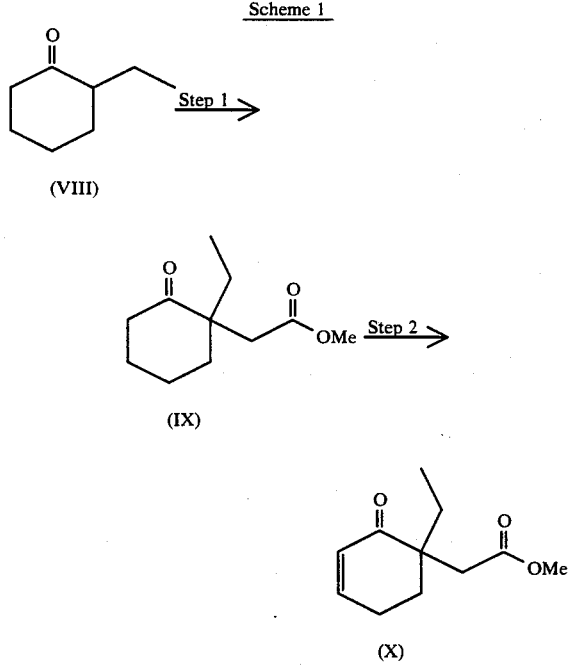

Step (1) a.KH/THF b. Et₃B c. BrCH₂COOCH₃
Step (2) a.PhSeCl/EtOAc b. H₂O₂/THF

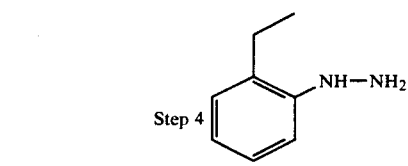

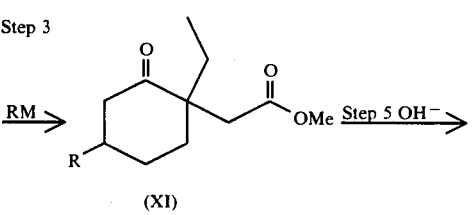

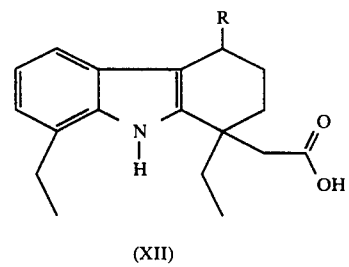

In Scheme 1, Step 1, 2-ethylcyclohexanone (VIII) was alkylated with methyl bromoacetate according to the procedure of E. Negishi et al. Tet. Lett. 24, 1341 (1983) in the presence of potassium hydride, and triethylborane in tetrahydrofuran. This afforded 1-ethyl-2-oxocyclohexaneacetic acid methyl ester (IX) in 45% yield. Compound (IX) was previously reported in Asselin et al., J. Med. Chem., 19, 787 (1976). About 5-10% of the 2,6 regioisomer was also formed which was separated by flash chromatography.

Conversion of (IX) to 1-ethyl-2-oxo-3-phenyl-selenocyclohexaneacetic acid methyl ester with benzeneselenenyl chloride according to the procedure of K. B. Shapless et al., J. Amer. Chem. Soc. 95, 6137 (1973) and oxidative elimination with hydrogen peroxide in Step 2 led to the required enone (X) in 55-68% yield in a one pot conversion.

Conjugate addition of organometallic reagents RM to (X) in Step 3 wherein R is PhCH₂— or CH₂=CH—CH₂— and m is MgCl or SiMe₃ gave tri-substituted ketone (XI) as a mixture of diastereomers. Fischer indole cyclization with 2-ethylphenylhydrazine in Step 4 and subsequent base hydrolysis in Step 5 gave tetrahydrocarbazoles (XII). The diastereomers, which represent another aspect of the invention, can be separated either before or after cyclization.

TABLE 1

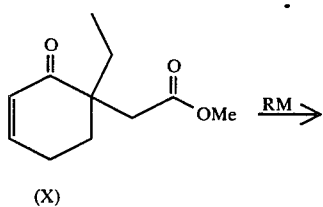

(X)

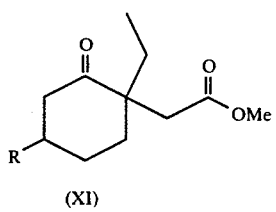

(XI)

| Entry | RM | % of Yield of (XI) | Ratio of Isomers |
|---|---|---|---|
| 1 | PhCH$_2$MgCl | 69 | 1:1 to 1.5:1 |
| 2 | CH$_2$:CHCH$_2$SiMe$_3$ | 82 | 13:1 |

Conjugate addition reactions of organometallic reagents RM to (X) in Step 3 gave a 1:1 to a 1.5:1 mixture of diastereomers when carried out at −40° C. in tetrahydrofuran (THF) by adding an ether or THF solution of the Grignard reagent (1 to 1.4 equivalents) to a solution of (X) in THF/Me$_2$S containing 0.1 equivalents of copper bromide dimethyl sulfide complex [(K. J. Shea et al. Tetrahedron Lett., 24, 1003 (1983)]. See Table 1, Entry 1. When allyltrimethylsilane was added to (X) in the presence of titanium tetrachloride [(H. Sakurai, Pure Appl., Chem., 54, 1 (1982)] a 13:1 mixture of diastereomers as evidenced by capillary GC, analytical HPLC and 200 MHz NMR was obtained. The major diastereomer was cis.

The ketones (XI) were then subjected to Fischer indole synthesis conditions in Step 4 by refluxing with 2-ethylphenylhydrazine in methanol the appropriate time to form the hydrazone (See Table 2). The hydrazone solution was then cooled to 0° C., treated with acetyl chloride to generate HCl and refluxed an additional 45 minutes to affect Fischer indole cyclization. The esters were then hydrolyzed in Step 5 with potassium carbonate in aqueous methanol to afford tetrahydro-1-H-carbazole-1-acetic acids (XII).

TABLE 2

| R | hours for hydrazone (VII) formation | % yield of ester | % yield of (XII) |
|---|---|---|---|
| CH$_2$:CHCH$_2$ | 120 | 40 | 75 |
| PHCH$_2$ | 112 | 31[a] | 79[a] |

[a]The mixture of diastereomers was separated by reverse phase HPLC at the indole acetic acid stage.

Compounds of formula (I) where R$^9$=lower alkyl can also be prepared by treating an ester of compound (I), where R$^9$=H, with sodium hydride or potassium hydride in a suitable solvent followed by treatment with an alkyl halide followed by hydrolysis of the ester.

The requisite starting materials of formula (VI), phenylhydrazine or substituted phenylhydrazines are known or are prepared according to known methods. A convenient method for preparing the substituted phenylhydrazines involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry," Reinhold Publishing Corporation, New York, 1961, p. 734.

The requisite starting materials of formula (IX) are prepared by several methods. At least three of these methods are illustrated in Asselin et al., U.S. Pat. No. 4,057,559.

The above starting materials of formula (V) and formula (VI) are used to prepare the compounds of this invention in the following manner:

The starting material of formula (VI) is condensed with substantially one molar equivalent of the starting material of formula (V) to give the corresponding hydrazone of formula (VII) in which R$^1$ to R$^9$ inclusive and m and n are as defined hereinbefore.

Generally speaking, the condensation is performed preferably in an inert atmosphere, for example, nitrogen or argon. The condensation can be carried out in the absence of a solvent, but it desired, a suitable solvent may be selected from the group consisting of the lower alkanols such as methanol and ethanol; aromatics such as benzene and toluene; the ethers, such as tetrahydrofuran, diethyl ether, dioxane, bis(2-methoxyethyl)-ether and the like; and the halogenated hydrocarbons, methylene chloride, chloroform and the like. Methanol, ethanol and toluene are practical solvents. Times and temperatures for the condensation generally range from 5 minutes to five or six days at 0° to 100° C. Convenient time and temperature ranges include 20° C. to the boiling point of the mixture and 15 minutes to 130 hours. Preferably, the reaction is run without solvent.

The resulting hydrazone (VII) is then cyclized to the tricyclic ester of formula (I) by the action of a suitable cyclization agent according to the conditions of the "Fischer Indole Synthesis," for example, see B. Robinson, Chem. Rev. 63, 373 (1963).

A variety of cyclization agents are effective for this cyclization, some of the agents suitable for this cyclization include p-toluenesulfonic acid, hydrogen chloride or hydrogen chloride generated from acetyl chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide and aniline salts. In other words the usual catalysts employed for the "Fischer Indole Synthesis" are efficacious; however, the preferred cyclization agent is a solution of boron trifluoride etherate in acetic acid.

In practice the isolation of the hydrazone (VII) from the condensation reaction mixture is optional. Accordingly, the cyclization agent is added either to the above condensation reaction mixture containing the hydrazone, or to the isolated hydrazone optionally dissolved in one of the above solvents, whereby the hydrazone then cyclizes to give the corresponding tricyclic ester of formula (I) in which R$^1$ to R$^9$ inclusive and m and n are as defined hereinbefore.

The cyclization usually proceeds smoothly and rapidly. Convenient reaction times for the cyclization include five minutes to two hours, preferably 30 minutes to one hour. Convenient temperatures include 20° to 200° C., preferably 120° to 180° C.

In practice a most convenient and practical procedure for effecting the above cyclization comprises evaporating solvent from the condensation reaction mixture containing the hydrazone if a solvent was used, and then heating the hydrazone at reflux in a solution of boron trifluoride etherate in acetic acid.

The starting material of formula (V) may be either a cycloalkanoneacetic acid derivative or its corresponding lower alkyl ester ($R^7$=lower alkyl). Accordingly, when the acid is employed, the above process yields the tricyclic compound identical to the desired compound of formula (I) and when the starting material is lower alkyl ester the above process yields the lower alkyl ester tricyclic compound of formula (I).

The subsequent conversion of the lower alkyl ester tricyclic compound of formula (I) to the corresponding compound of formula (I) is effected readily by subjecting the tricyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, (pp. 615–617) are also applicable.

For basic hydrolysis a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product.

An alternate process for the production of compounds of structure (I)

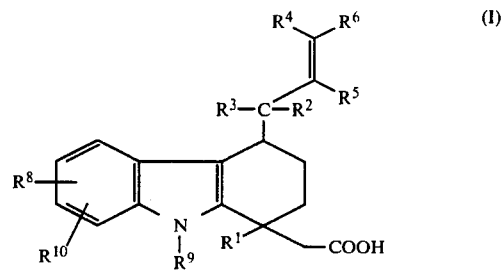

wherein $R^1$, $R^2$, $R^3$, $R^4$, $R^5$ and $R^6$ are hydrogen or lower alkyl, $R^8$ and $R^{10}$ are independently hydrogen, lower alkyl or halogen, $R^9$ is hydrogen or lower alkyl, comprises (a) reacting the compound of structure (IV)

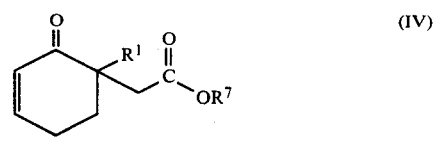

wherein $R^1$ is as defined above and $R^7$ is lower alkyl with

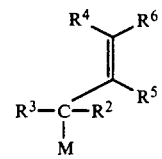

wherein $R^2$, $R^3$, $R^4$, $R^5$ and $R^6$ are as defined above and M may be $SiMe_3$ or $SnBu_3$ with the reaction being carried out in the presence of an acid, or M may be MgBr, MgCl or MgI with the reaction being carried out in the presence of a suitable copper catalyst, to obtain a compound or compounds of structure Va, Vb, Vc or Vd

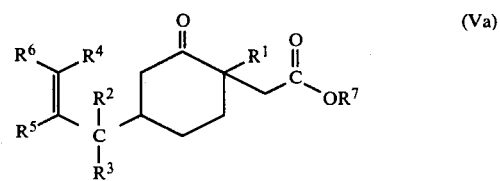

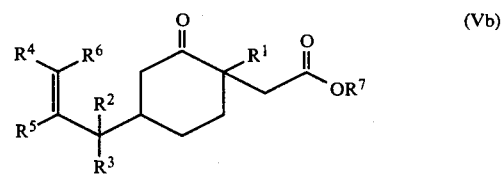

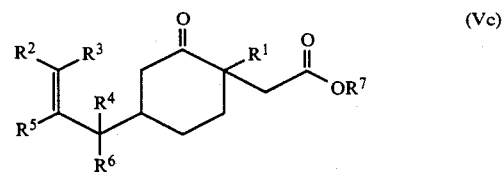

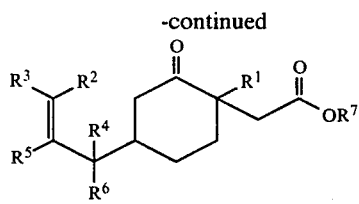

wherein $R^1$, $R^2$, $R^3$, $R^4$, $R^5$, $R^6$ and $R^7$ are as defined above and (b) reacting a compound of structure Va, Vb, Vc or Vd with a suitable oxidizing agent such as sodium periodate in the presence of osmium tetroxide in aqueous tetrahydrofuran to form a compound of structure (XIII)

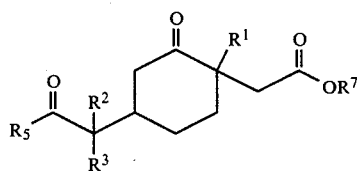

wherein $R^1$, $R^2$, $R^3$, $R^5$ and $R^7$ are as defined above (c) reducing the compound of structure (XIII) with a suitable reducing agent such as $LiAl[OC(C_2H_5)_3]H$ in tetrahydrofuran to form a compound of structure (XIV)

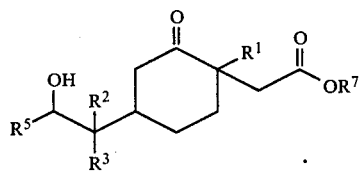

wherein $R^1$, $R^2$, $R^3$, $R^5$ and $R^7$ are as defined above (d) acetylating the compound of structure (XIV) with acetic anhydride or acetyl chloride in an appropriate solvent such as methylene chloride containing an amine base or pyridine to form a compound of structure (XV)

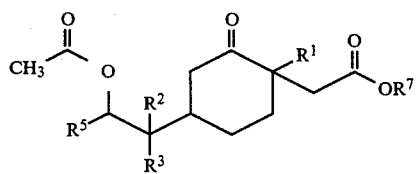

wherein $R^1$, $R^2$, $R^3$, $R^5$ and $R^7$ are as defined above (e) reacting the compound of structure (XV) with a hydrazine of structure (VI)

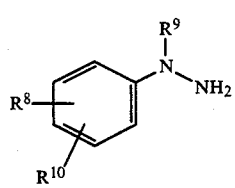

wherein $R^8$ and $R^{10}$ are independently hydrogen, lower alkyl or halogen and $R^9$ is hydrogen or lower alkyl to form a compound of structure (XVI)

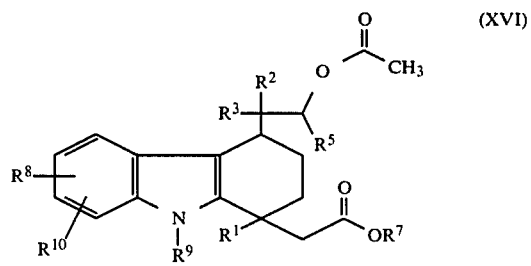

wherein $R^1$, $R^2$, $R^3$, $R^5$, $R^7$, $R^8$, $R^9$ and $R^{10}$ are as defined above (f) hydrolyzing the compound of structure (XVI) to remove the acetate group and forming the compound of structure (XVII)

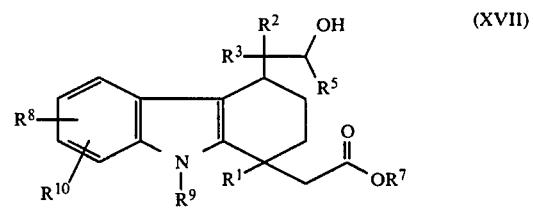

wherein $R^1$, $R^2$, $R^3$, $R^5$, $R^7$, $R^8$, $R^9$ and $R^{10}$ are as defined above (g) oxidizing the alcohol of structure (XVII) to obtain the compound of structure (XVIII)

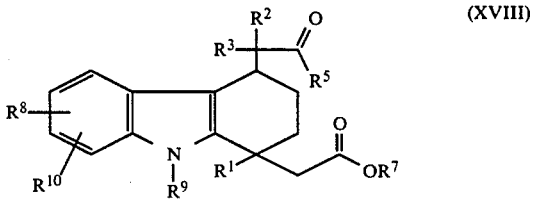

wherein $R^1$, $R^2$, $R^3$, $R^5$, $R^7 R^8$, $R^9$ and $R^{10}$ are as defined above (h) reacting the compound of strucure (XVIII) with the compound of structure (XIX)

wherein $R^4$ and $R^6$ are independently hydrogen or lower alkyl affording the ester of compound (I), and further hydrolyzing said ester to obtain the compound (I).

Alternatively, the compound of structure (XIV)

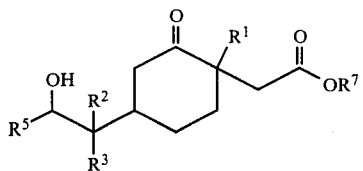

wherein $R^1$, $R^2$, $R^3$ and $R^5$ are hydrogen or lower alkyl and $R^7$ is lower alkyl can be reacted directly with a hydrazine of structure (VI)

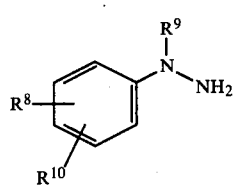

wherein $R^8$ and $R^{10}$ are independently hydrogen, lower alkyl or halogen and $R^9$ is hydrogen or lower alkyl to form the compound of structure (XVII)

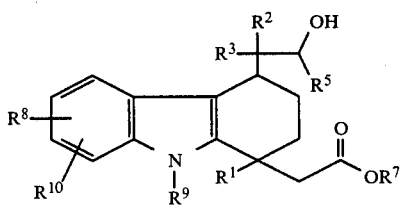

wherein $R^1$, $R^2$, $R^3$, $R^5$, $R^7$, $R^8$, $R^9$ and $R^{10}$ are as defined above.

The following examples further illustrate this invention.

EXAMPLE 1 cis-1,8-Diethyl-2,3,4,9-tetrahydro-4-(2-propenyl)-1H-carbazole-1-acetic Acid (XII, R=—CH$_2$—CH=CH$_2$)

(a) Preparation of 2-Ethylcyclohexanone (VIII)

2-Ethylcyclohexanol (1.6 moles, 204 g, 226 mL) was stirred in 3.2 l of acetone at 0° C. and treated with 8N Jones reagent (prepared from 106.8 g of CrO$_3$ suspended in 92 mL of concentrated sulfuric acid and diluted to 400 mL with water) until the orange color persisted (~430 mL). Isopropanol was then added to turn the solution green again after which it was poured into 2 l of ether. The product was washed with 6×500 ml of brine, dired over MgSO$_4$ and stripped of solvent. Short path distillation (b.p. 80°–85° C. at 25 mm) afforded 184 g (1.46 moles, 91%) of 2-ethylcyclohexanone as a colorless oil.

(b) Preparation of 1-Ethyl-2-oxocyclohexaneacetic Acid Methyl Ester (IX)

According to the procedure of E. Negishi and S. Chatterjee, Tet. Lett., 24, 1341 (1983), potassium hydride (417 mmol, 70 mL, ~6M in mineral oil) was placed under nitrogen in a three-necked flask equipped with a mechanical stirrer and was washed three times with petroleum ether (this washing can be omitted). Tetrahydrofuran (200 mL, distilled from sodium/Ph$_2$CO) was then added followed by a solution of 2-ethylcyclohexanone (VIII) (50 g, 396 mmol) in 200 mL of tetrahydrofuran added as a slow stream over ~15 minutes. The addition was followed one minute later by 495 mL of 1M Et$_3$B in tetrahydrofuran followed 1 hour later by 594 mmol (91 g, 56 mL) of methyl bromoacetate. The yellow suspension was stirred for 2.5 hours, poured into 800 mL of water (being careful to decant away from excess KH!) and extracted with 4×300 mL of petroleum ether. The combined organic phases were dried over sodium sulfate and concentrated in vacuo. The product was distilled through a 6 inches Vigreux column collecting the material boiling at 107°–118° C. at 0.8 mm (the two regioisomers from the alkylation). This material was then purified by flash chromatography (4 inches diameter column, 7.5% ethyl acetate in petroleum ether eluent, 5½ inches of silica gel) to afford 35.33 g (178.2 mmol, 45%) of colorless oil. The desired product is the lower R$_f$ material of the two overlapping spots on thin layer. R$_f$=0.23 in 10% ethyl acetate/petroleum ether. About 5–10% of the 2,6 regioisomer can be isolated as the top spot.

(c) Preparation of 1-Ethyl-2-oxocyclohex-3-eneacetic Acid Methyl Ester (X)

The ketone, 2-carbomethoxymethyl-2-ethylcyclohexanone (IX) (141 mmol, 28 g) was stirred in 1.25 l of ethyl acetate (dried over 3A molecular sieves) and treated with 169 mmol (32.5 g) of PhSeCl. The reaction was stirred under nitrogen for 4 hours then treated with 250 mL of water. The mixture was shaken vigorously in a separatory funnel and the organic phase was returned to the reaction flask. Tetrahydrofuran (550 mL) was then added followed by 35 mL of 30% H$_2$O$_2$(aq.) added dropwise. The reaction mixture was stirred for one hour then washed with 500 mL of water and 500 ml of saturated Na$_2$CO$_3$ (aq.). The product was then dried over MgSO$_4$ and concentrated in vacuo. Flash chromatography (4 inches diameter column, 20% ethyl acetate in petroleum ether eluent, 5½ inches of silica gel) afforded 15.3 g (78.0 mmol, 55%) of the product as a pale yellow oil. R$_f$=0.9 in 15% ethyl acetate/petroleum ether on TLC.

(d) Preparation of cis-1-Ethyl-2-oxo-4-(2-propenyl)cyclohexaneacetic Acid Methyl Ester (XI, R=CH$_2$—CH=CH$_2$)

The enone, 6-carbomethoxymethyl-6-ethyl-2-cyclohexen-1-one (X) (81.53 mmol, 16.0 g) was stirred in 82 mL of dry CH$_2$Cl$_2$ (distilled from CaH$_2$) at −78° C. under nitrogen and treated dropwise with 122.30 mmol (23.2 g) of TiCl$_4$ followed by 97.84 mmol (11.18 g, 15.55 mL) of allyltrimethylsilane. After 1.5 hours, the reaction was quenched at −78° C. with 50 mL of MeOH, poured into 200 mL of water and extracted with 4×100 mL of ether. Drying (Na$_2$SO$_4$) and flash chromatography (95 mm column, 15% EtOAc/petroluem ether eluent, 5½ inches of silica gel) afforded 16.02 g (67.2 mmol, 82%) of colorless oil. The product appeared to be predominately one diastereomer in at least a 9:1 ratio, the major diastereomer being cis. R$_f$=0.39 in 15% ethyl acetate/petroleum ether on TLC.

(e) Preparation of cis-1,8-Diethyl-2,3,4,9-tetrahydro-4-(2-propenyl)-1H-carbazole-1-acetic Acid Methyl Ester (XII, R=CH$_2$—CH=CH$_2$, methyl ester)

The ketone, cis-1-ethyl-2-oxo-4-(2-propenyl)cyclohexaneacetic acid methyl ester (XI, R=CH$_2$—CH=CH$_2$) (51.14 mmol, 12.188 g) and the 2-ethylphenylhydrazine (51.14 mmol, 6.965 g) were refluxed in 219 mL of MeOH for 120 hours. The reaction was cooled to 0° C., treated with 102 mmol (8.0 g, 7.3 mL) of AcCl and refluxed for an additional 45 minutes. Solvent removal and flash chromatography (95 mm column, 12% EtOAc/petroleum ether eluent, 5½ inches of silica gel) afforded 7.0 g (20.64 mmol, 40%) of orange oil. $R_f=0.54$ in 15% ethyl acetate/petroleum ether on TLC.

(f) Preparation of cis-1,8-Diethyl-2,3,4,9-tetrahydro-4-(2-propenyl)-1H-carbazole-1-acetic Acid (XII, R=CH$_2$—CH=CH$_2$)

The ester, cis-1,8-diethyl-2,3,4,9-tetrahydro-4-(2-propenyl)-1H-carbazole-1-acetic acid methyl ester (XII, R=CH$_2$—CH=CH$_2$, methyl ester) (20.64 mmol, 7.007 g) and K$_2$CO$_3$ (24.77 mmol, 3.423 g) were refluxed in 165 mL of MeOH containing 21 mL of water under nitrogen for 27.5 hours. Most of the MeOH was removed in vacuo and the residue was dissolved in 50 mL of water. The solution was acidified to pH ~1 with 3M HCl (aq.) and extracted with 4×50 mL of Et$_2$O. The combined organic solutions were dried over MgSO$_4$ and concentrated. Flash chromatography (75 mm column, 40% EtOAc/petroleum ether eluent, 5½ inches of silica gel) afforded 5.0152 g (15.41 mmol, 75%) of yellow oil. Liquid chromatography showed that the product was predominately one isomer in at least a ~9:1 ratio, the major diastereomer being cis. Three grams of the compound were recrystallized from 20 mL of 2:1 petroleum ether/benzene to afford 1.3 g of off-white needles (m.p. 121°-124° C.). A liquid chromatogram of the recrystallized material indicated 99.3% purity and a second crop was 97.6% pure.

NMR(CDCl$_3$/TMS): δ 0.8(t, 3H, J=8, CH$_2$CH$_3$), 1.33(t, J=8, 3H, ArCH$_2$CH$_3$), 1.6-2.5 (m, 6H, CH$_2$CH$_3$, ring CH$_2$), 2.5-3.4(m, 7H, CH, CH$_2$COO, ArCH$_2$CH$_3$, C=CCH$_2$), 4.9-5.3(m, 2H, C=CH$_2$), 5.6-6.3(m, 1H, CH=CH$_2$), 7.0-7.6(m, 3H, aromatics), 8.98(broad s, 1H, NH).

IA(KBr): 3600-3100 (OH), 3400 (NH), 1710 (C=O).

EXAMPLE 2

1,8-Diethyl-2,3,4,9-tetrahydro-4-(phenylmethyl)-1H-carbazole-1-acetic Acid (XII, R=phenylmethyl)

(a) Preparation of 1-Ethyl-2-oxo-4-(phenylmethyl)cyclohexaneacetic Acid Methyl Ester (XI, R=PhCH$_2$)

The enone, 1-ethyl-2-oxocyclohex-3-eneacetic acid methyl ester (X), prepared by the process of Example 1, Step (c), (56.26 mmole, 11.04 g), Me$_2$S (11.25 mL) and 5.626 mmol (1.15 g) of CuBr.Me$_2$S were stirred in 165.5 mL of THF at −40° C. under nitrogen and treated with 56.26 mmol (28.1 mL of 2M in THF) of PhCH$_2$MgCl added dropwise. The reaction was then quenched with 150 mL of 1M HCl and extracted with 4×100 mL of petroleum ether. The organic phases were dried over Na$_2$SO$_4$ and concentrated. Flash chromatography (95 mm column, 12% ethyl acetate/petroleum ether eluent) afforded 11.20 g (38.84 mmol, 69%) of yellow oil as a mixture of isomers.

Preparation of 1,8-Diethyl-2,3,4,9-tetrahydro-4-(phenylmethyl)-1H-carbazole-1-acetic Acid Methyl Ester (XII, R=PhCH$_2$, methyl ester)

The mixture of isomeric ketones prepared in Step (a), (74.56 mmol, 17.775 g) and the 2-ethylphenylhydrazine (74.56 mmol, 10.156 g) were refluxed in 320 mL of MeOH under nitrogen for 112 hours. The reaction was cooled to 0° C., treated with 112 mmol (8.78 g, 8 mL) of AcCl and refluxed an additional 45 minutes. The reaction was then concentrated in vacuo and flash chromatography (95 mm column, 12% EtOAc/petroleum ether eluent, 5½ inches of silica gel) afforded 8.922 g (22.9 mmol, 31%) of yellow oil as a mixture of isomers.

(c) Preparation of 1,8-Diethyl-2,3,4,9-tetrahydro-4-(phenylmethyl)-1H-carbazole-1-acetic (XII, R=PhCH$_2$)

The isomeric esters obtained in Step (b), (22.9 mmol, 8.922 g) and K$_2$CO$_3$ (27.48 mmol, 3.798 g) were heated at reflux in 183 mL of MeOH and 23 mL of water under nitrogen for 26.5 hours. Most of the MeOH was removed in vacuo and the residue was dissolved in 50 mL of water. The solution was acidified to pH ~1 with 3M HCl (aq.), extracted with 4×50 mL of ether, dried over MgSO$_4$ and concentrated. Flash chromatography (75 mm column, 50% EtOAc/petroleum ether eluent, 5½ inches of silica gel) afforded 6.7712 g (18.03 mmol, 79%) of yellow oil. About 1 g of each isomer was separated using reverse phase (C$_{18}$) chromatography and each was recrystallized from ~2/1 petroleum ether/benzene as white crystals. Both isomers were dried in vacuo (72° C., silica gel desiccant) for 8 hours. The first isomer eluted by reverse phase chromatography (60/40 CH$_3$Cl/H$_2$O) with 0.001M KH$_2$PO$_4$) was designated the A isomer and had m.p. 185°-186° C. The second eluted isomer was designated the B isomer and had m.p. 181°-184° C.

A isomer:

NMR (CDCl$_3$/TMS): δ 0.9 (t, 3H, J=9, CH$_2$CH$_3$), 1.36 (t, 3H, J32 9, ArCH$_2$CH$_3$), 1.5-2.3 (m, 7H, ring CH$_2$ and CH), 2.6-3.6 (m, 6H, PhCH$_2$, ArCH$_2$, CH$_2$COO), 7.0-7.6 (m, 8H, aromatics), 8.9 (broad s 1H, NH).

IR (KBr): 3440 (NH), 3600-3000 (OH), 3060 (CH aromatic), 3000-2880 (CH aliphatic), 1710 (C=O).

B isomer:

NMR (CDCl$_3$/TMS): δ 0.88 (t, J=9, 3H, CH$_2$CH$_3$), 1.36 (t, J=9, 3H, ArCH$_2$CH$_3$), 1.6-2.2 (m, 7H, ring CH$_2$ and CH), 2.7-3.5 (m, 6H, PhCH$_2$, ArCH$_2$, CH$_2$COO), 6.9-7.6 (m, 8H, aromatics), 9.0 (broad s, 1H, NH).

IR (KBr): 3600-2500 (OH), 3420 (NH), 1700 (C=O).

EXAMPLE 3 cis-1-Ethyl-2,3,4,9-tetrahydro-4-(2-propenyl)-1H-carbazole-1-acetic Acid (III, R$^4$, R$^5$, R$^6$, R$^8$=H)

(a) Preparation of cis-1-Ethyl-2,3,4,9-tetrahydro-4-(2-propenyl)-1H-carbazole-1-acetic Acid Methyl Ester Five grams (20.98 mmol) of cis-1-ethyl-2-oxo-4-(2-propenyl)cyclohexane-acetic acid methyl ester, prepared by the process of Example 1, Step (d), and 2.27 g (21 mmol, 2.07 mL) of 2-phenylhydrazine were heated at reflux under nitrogen in 21 mL of toluene with azeotropic removal of water. After 24 hours, the toluene was removed in vacuo and the residue was dissolved in 15 mL of acetic acid. It was treated with 27.27 mmol (3.87 g, 3.35 mL) of boron trifluoride etherate and refluxed under nitrogen for 20 minutes. The reaction mixture was poured into 40 mL of water and extracted with 4×40 mL of ether. The combined organic phases were washed with 2×20 mL of saturated sodium bicarbonate (aq.) and dried over magnesium sulfate. Flash chromatography (75 mm column, 7% ethyl acetate in petroleum ether eluent, 5½ inches of silica gel) afforded 3.04 g (9.81 mmol, 47%) of an orange oil. $R_f=0.65$ in 15% EtOAc/petroleum ether.

IR (neat): 3490 (NH), 2850-3050 (CH), 1715 (C=O).

NMR (CDCl₃/TMS), 200 MHz): δ 0.836(t, J=7.5, 3H, CH₂C$\underline{H}_3$), 1.258(t, J=7.15, 3H, ArCH₂C$\underline{H}_3$), 1.6–2.4, 2.$\overline{6}$–2.8 (m, 8H, C$\underline{H}_2$CH₃, (C$\underline{H}_2$C$\underline{H}_2$C, C=CHC$\underline{H}_2$), 2.664 (5.2H, C$\underline{H}_2$COOMe), 3.05 (m, C=CHC$\overline{H}_2$CH), 3.703 (s, 3H, $\overline{O}$CH₂), 5.0–5.1 (m, 2H, C=CH₂), 5.8–$\overline{6}$.0 (m, 1H, H₂C=C$\underline{H}$), 7.0–7.6 (m, 4H, aromatics), 9.3 (broad s, 1H, NH).

(b) Preparation of cis-1-Ethyl-2,3,4,9-tetrahydro-4-(2-propenyl)-1H-carbazole-1-acetic Acid A solution of the ester, cis-1-ethyl-2,3,4,5-tetrahydro-4-(2-propenyl)-1H-carbazole-1-acetic acid methyl ester (9.71 mmol, 3.01 g) and potassium carbonate (14.57 mmol, 2.01 g) were refluxed under nitrogen for 24 hours in 78 mL of methanol and 9.7 mL of water. Most of the methanol was removed in vacuo and the residue was suspended in 15 mL of water. It was acidified to pH=1 with 1M hydrochloric acid and extracted with 4×60 mL of ether. The combined ether layers were dried over magnesium sulfate and concentrated. Flash chromatography (50 mm diameter column, 25% ethyl acetate in petroleum ether eluent, 5½ inches of silica gel) afforded 2.72 g (9.19 mmol, 95%) of oily product which was crystallized from 85:15 petroleum ether:benzene to afford 2.2 g of off-white powder. This powder was dried at 78° C. over phosphorous pentoxide for 7 hours and had m.p. 103°–105° C.

Anal. Calcd.: C, 76.74%; H, 7.79%; N, 4.71%. Found: C, 76.84%; H, 7.70%; N, 4.73%.

IR (KBr): 3420 (NH), 3600–3000 (OH), 2860–3100 (—CH), 1715 (C=O).

Examples 5–8, 10, 11, 13–20, 22, 25, 28–32, 34, 36, 38–40, and 42 were prepared by treating cis-1-ethyl-2-oxo-4-(2-propenyl)cyclohexaneacetic acid methyl ester (Example 1, Step d) with the appropriate aryl-hydrazine in refluxing toluene for 12–100 hours to form the hydrazone of structure VII, concentration in vacuo, and dissolution in acetic acid. Treatment with boron trifluoride etherate and refluxing for 5–60 minutes afforded the compounds of structure I as their methyl esters. These were then hydrolyzed with sodium hydroxide in aqueous ethanol to afford compounds of structure I.

Example 4 was prepared by treating trans-1-ethyl-2-oxo-4-(2-propenyl)cyclohexaneacetic acid methyl ester (prepared as in Example 1, Step d, except that aluminum trichloride was used instead of titanium tetrachloride, the reaction was carried out at 0° C. to room temperature and the trans isomer was separated from the cis isomer by chromatography on silica gel) with 2-ethylphenylhydrazine and subsequent hydrolysis as described for Examples 5–8, 10, 11, 13–20, 22, 25, 28–32, 34, 36, 38–40, and 42.

Examples 9 and 12 were prepared by treating 1-methyl-2-oxo-4-(2-propenyl)cyclohexaneacetic acid methyl ester (prepared as in Example 1, Step d except that 2-methylcyclohexanone was used as the starting material in Example 1, Step b instead of 2-ethylcyclohexanone) with the appropriate hydrazine and subsequent hydrolysis as described for Examples 5–8, 10, 11, 13–20, 22, 25, 28–32, 34, 36, 38–40 and 42.

Example 21 was prepared like examples 9 and 12 starting from 2-propylcyclohexanone instead of 2-methylcyclohexanone.

Example 23 and 35 were prepared by treating 4-(1,1-dimethyl-2-propenyl)-1-ethyl-2-oxocyclohexaneacetic acid methyl ester (prepared as in Example 1, Step d except that (3-methyl-2-butenyl)-tributyltin was used in place of allyltrimethylsilane) with the appropriate hydrazine and subsequent hydrolysis as described for Examples 5–8, 10, 11, 13–20, 22, 25, 28–32, 34, 36, 38–40 and 42.

Examples 24 and 41 were prepared like examples 23 and 35 except that (2-methyl-2-propenyl)-tributyltin was used instead of (3-methyl-2-butenyl)tributyltin.

Examples 26 and 27 were prepared by treating 1-ethyl-2-oxo-4-(phenylmethyl)cyclohexaneacetic acid methyl ester (Example 2, Step a) with phenylhydrazine and subsequent hydrolysis as described for Examples 5–8, 10, 11, 13–20, 22, 25, 28–32, 34, 36, 38–40 and 42.

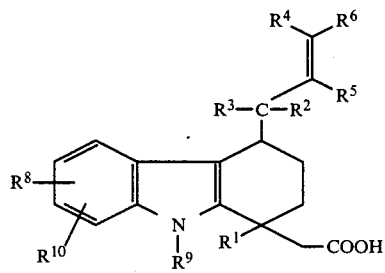

| Example | R¹ | R² | R³ | R⁴ | R⁵ | R⁶ | R⁸ | R⁹ | R¹⁰ | Configuration | Melting Point |
|---|---|---|---|---|---|---|---|---|---|---|---|
| 4 | Et | H | H | H | H | H | 8-Et | H | H | trans | 127–129 |
| 5 | Et | H | H | H | H | H | 8-nPr | H | H | cis | 140–142 |
| 6 | Et | H | H | H | H | H | 6-Et | H | H | cis | 110–113 |
| 7 | Et | H | H | H | H | H | 7-Et | H | H | cis | 95–97 |
| 8 | Et | H | H | H | H | H | 6-nBu | H | H | cis | 88–90 |
| 9 | Me | H | H | H | H | H | 8-Et | H | H | — | 124–126 |
| 10 | Et | H | H | H | H | H | 8-iPr | H | H | cis | 149–150 |
| 11 | Et | H | H | H | H | H | 8-Me | H | H | cis | 142–143 |
| 12 | Me | H | H | H | H | H | H | H | H | — | 89–91 |
| 13 | Et | H | H | H | H | H | 6-F | H | H | cis | 134–135 |
| 14 | Et | H | H | H | H | H | 8-Br | H | H | cis | 143–146 |
| 15 | Et | H | H | H | H | H | 8-F | H | H | cis | 112–115 |
| 16 | Et | H | H | H | H | H | 8-Cl | H | H | cis | 120–121.5 |
| 17 | Et | H | H | H | H | H | 5-Cl | H | H | cis | 172.5–174 |
| 18 | Et | H | H | H | H | H | 7-Br | H | H | cis | 108.5–110.5 |
| 19 | Et | H | H | H | H | H | 5-Br | H | H | cis | 159–160.5 |
| 20 | Et | H | H | H | H | H | 7-Cl | H | H | cis | 113–115 |

-continued

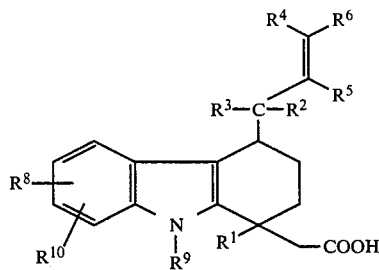

| Example | $R^1$ | $R^2$ | $R^3$ | $R^4$ | $R^5$ | $R^6$ | $R^8$ | $R^9$ | $R^{10}$ | Configuration | Melting Point |
|---|---|---|---|---|---|---|---|---|---|---|---|
| 21 | nPr | H | H | H | H | H | 8-Et | H | H | — | 122–126 |
| 22 | Et | H | H | H | H | H | 8-I | H | H | cis | 157–159 |
| 23 | Et | Me | Me | H | H | H | 8-F | H | H | — | 121–122 |
| 24 | Et | H | H | H | Me | H | H | H | H | — | 124–126 |
| 25 | Et | H | H | H | H | H | 6-Cl | H | H | cis | 133–134 |
| 26 | Et | H | H | H | ⌒⌒ | | H | H | H | — | 115–116.5 |
| 27 | Et | H | H | H | ⌒⌒ | | H | H | H | — | 149.5–151.5 |
| 28 | Et | H | H | H | H | H | 6-Br | H | H | cis | 120–122 |
| 29 | Et | H | H | H | H | H | 7-F | H | 8-Me | cis | 160–161 |
| 30 | Et | H | H | H | H | H | 7-Cl | H | 8-Me | cis | 150.5–152.5 |
| 31 | Et | H | H | H | H | H | 5-Me | H | 8-Me | cis | 131–134 |
| 32 | Et | H | H | H | H | H | 7-Cl | H | 8-Cl | cis | 117.5–119 |
| 33 | Et | H | H | H | H | H | 5-Me | H | 8-Br | cis | 166–167.5 |
| 34 | Et | H | H | H | H | H | 5-Me | H | 8-Cl | cis | 161–163 |
| 35 | Et | Me | Me | H | H | H | 7-Cl | H | 8-Me | — | 137–141 |
| 36 | Et | H | H | H | H | H | 6-Cl | H | 8-Cl | cis | 136–137 |
| 37 | Et | H | H | H | H | H | 7-Br | H | 8-Me | cis | 138–139.5 |
| 38 | Et | H | H | H | H | H | 5-Cl | H | 8-Me | cis | 179–182 |
| 39 | Et | H | H | H | H | H | 5-F | H | 8-Me | cis | 159–160 |
| 40 | Et | H | H | H | H | H | 5-Cl | H | 8-Cl | cis | 155–156 |
| 41 | Et | H | H | H | Me | H | 7-Cl | H | 8-Me | — | 128–129.5 |
| 42 | Et | H | H | H | H | H | 5-Cl | H | 7-Cl | cis | 170–172 |
| 43 | Et | H | H | H | H | H | 8-Et | $CH_3$ | H | cis | 181–183 |
| 44* | Et | H | H | H | H | H | 8-Et | H | H | 1R-cis | 133.5–134 |
| 45* | Et | H | H | H | H | H | 8-Et | H | H | 1S-cis | 133–134 |
| 46 | Et | H | H | H | H | H | 5-Et | H | 8-Cl | cis | 149–150 |
| 47 | Et | H | H | H | H | H | 5-Br | H | 8-Me | cis | 176–178 |
| 48 | Et | H | H | Me | H | H | 8-Me | H | H | cis | 120–121 |
| 49 | Et | H | H | H | H | H | 7-F | H | 8-F | cis | 105–107 |
| 50 | Et | H | H | H | ⌒⌒ | | 7-Cl | H | 8-Me | — | 158–159 |
| 51 | Et | H | H | H | ⌒⌒ | | 7-Cl | H | 8-Me | — | 198–200 |
| 52 | Et | H | H | H | ⌒⌒ | | 8-Me | H | H | — | 121–123 |
| 53 | Et | H | H | H | ⌒⌒ | | 8-Me | H | H | — | 179–181 |
| 54* | Et | H | H | H | H | H | 7-Cl | H | 8-Et | cis | 142–144 |

*salt with benzenemethanamine (1:1)

| Example | Phenylquinone Writhing in Mice* | Paw Pressure Test in the Rat* | Preventative Adjuvant Edema* |
|---|---|---|---|
| 4 | 9% (100) | 0.02 | 35% (25) |
| 5 | 28.7 | 0.009 | 39% (25) 29% (10) |
| 6 | 103 | 0.01 | 21% (25) 36% (10) |
| 7 | 10 | 0.01 | 36% (25) |
| 8 | 10.6 | 0.2 | 56% (5) |
| 9 | 37% (25) | — | 38% (25) |
| 10 | 27% (25) | — | 43% (25) |
| 11 | 8.3 | 0.33 | 8.5 |
| 12 | 18.7 | 1.9 | 6.0 |
| 13 | 20% (25) | — | 36% (25) |
| 14 | 38% (25) | — | 28 |
| 15 | 27% (25) | — | 13.3 |
| 16 | 11 | 0.89 | 13 |
| 17 | 35% (25) | — | 6.6 |
| 18 | 3.8 | 0.00002 | 17.5 |
| 19 | 52% (25) | — | 50% (25) |
| 20 | 5.1 | 0.38 | 5.4 |
| 21 | 21% (25) | — | 24% (25) |
| 22 | 17 | — | 46% (25) |
| 23 | 41% (25) | — | 16% (25) |
| 24 | 29% (25) | — | 56% (25) |
| 25 | 45% (25) | — | 52% (25) |
| 26 | 4% (25) | — | 42% (25) |
| 27 | 1.2 | 0.12 | 49% (25) |
| 28 | 48% (25) | — | 35% (25) |
| 29 | 12.3 | 0.1 | 6.4 |
| 30 | 2.6 | 0.007 | 15 |
| 31 | 2.3 | 0.3 | 42% (25) |
| 32 | 2.0 | 0.08 | 22% (25) |
| 33 | 4.5 | 0.93 | 27% (25) |
| 34 | 7.6 | 0.46 | 2.6 |
| 35 | 28% (25) | — | 30% (25) |
| 36 | 7.6 | — | 35% (25) |
| 37 | 3.0 | — | 34% (25) |
| 38 | 5.4 | — | 48% (25) |
| 39 | 7% (25) | — | 54% (25) |
| 40 | 53% (25) | — | 37% (25) |
| 41 | 94% (25) | — | 56% (25) |
| 42 | 70% (25) | — | 78% (25) |
| 43 | 32% (200) | 8 | — |
| 44 | 5% (25) | 30% (1); 40% (5) | 0% (25) |
| 45 | 94% (25) | 0.011 | 54% (25) |
| 46 | 3.9 | — | 44% (25) |
| 47 | 3.2 | — | 72% (25) |
| 48 | 22% (10) | — | 51% (25) |
| 49 | 30.4 | 0.85 | 96% (25) |
| 50 | 0% (10) | — | 0% (25) |
| 51 | 93% (10) | — | 31% (25) |
| 52 | 5% (10) | — | 24% (25) |
| 53 | 74% (10) | — | 43% (25) |
| 54 | — | — | — |

*The numbers quoted are either percent inhibition with the dose in mg/kg given in parentheses, or the $ED_{50}$ in mg/kg.

EXAMPLE 43 cis-1,8-Diethyl-2,3,4,9-tetrahydro-9-methyl-4-(2-propenyl)-1H-carbazole-1-acetic Acid (a) Preparation of cis-1,8-Diethyl-2,3,4,9-tetrahydro-9-methyl-4-(2-propenyl)-1H-carbazole-1-acetic Acid Methyl Ester Potassium hydride (5.59 mmol, 639 mg of a 35% suspension by weight in mineral oil) was washed under nitrogen with petroleum ether then stirred in 12.3 mL of THF at room temperature. cis-1,8-Diethyl-2,3,4,9-tetrahydro-4-(2-propenyl)-1H-carbazole-1-acetic acid, methyl ester, prepared in Example 1, step e) (2.0 g, 5.89 mmol) was then added and the bubbling solution was stirred for 10 minutes and then treated with 30 mmol of methyl iodide (4.36 g, 1.41 mL). Thin layer chromatography showed a trace of starting material remaining. KH was added until all of the starting material was consumed. The reaction was quenched with methanol then poured into water. It was extracted with ether, dried over MgSO4 and concentrated in vacuo. Flash chromatography afforded 1.71 g (4.84 mmol, 82%) of product in the form of an oil.

NMR (CDCl₃/TMS, 200 MHz): δ 1.8 (t, 3H, J=7), 1.2 (t, 3H, J=7), 1.6-3.2 (m, 13H), 3.5 (s, 3H), 4.0 (s, 3H), 5.0-5.15 (m, 2H), 5.8-6.0 (m, 1H), 6.9-7.0 (m, 2H), 7.4 (m, 1H).

A solution of the ester prepared in step (a) (4.84 mmol, 1.71 g), potassium carbonate (7.26 mmol. 1 g) and 4.8 mL of water were refluxed under nitrogen in 38 mL of methanol for 24 hours. Most of the methanol was removed on a rotavap and the residue was acidified with aqueous HCl. The solution was extracted 4× with ether and the combined ether layers were dried over MgSO4. Flash chromatography afforded 1.3 g (3.83 mmol, 80%) of yellow solid. The compound could be crystallized from 4:1 petroleum ether/benzene to afford white crystals m.p. 181°-183° C.

Anal. Calcd.: C, 77,84%; H, 8.61%; N, 4.13%. Found: C, 77.83%; H, 8.41%; N, 4.03%.

NMR (CDCl₃/TMS, 200 MHz); δ 1.8 (t, 3H, J=7), 1.35 (t, 3H, J=7), 1.7-3.2 (m, 13H), 4.0 (s, 3H), 5.0-5.2 (m, 2H), 5.8-6.0 (m, 1H), 7.0 (m, 2H), 7.4 (m, 1H)

IR (CHCl₃): 3100-2850 (CH), 1700 (C:O).

EXAMPLE 44

(1R-cis)-1,8-Diethyl-2,3,4,9-tetrahydro-4-(2-propenyl)-1H-carbazole-1-acetic Acid Benzenemethanamine Salt (1:1)

(a) Preparation of (1R-cis)-1,8-Diethyl-2,3,4,9-tetrahydro-4-(2-propenyl)-1H-carbazole-1-acetic Acid 2,3-Dimethoxy-strychnidin-10-one Salt (1:1)

Six millimoles (1.947 g) of cis-1,8-diethyl-2,3,4,9-tetrahydro-4-(2-propenyl)-1H-carbazole-1-acetic acid, prepared by the process of Example 1, step f), and 6.0 mmol (2.583 g) of 2,3-dimethoxy-strychnidin-10-one dihydrate (brucine dihydrate) were dissolved in 25 mL of hot ethanol. To the resultant clear solution was added 6.25 mL of water and the new solution was left standing at room temperature overnight. The white crystalline salt was collected by filtration and washed with a 1:1 ethanol-water mixture (5 mL). The mother liquor was used to isolate the other enantiomer in Example 45, Step a). This salt (1.94 g) was taken back in hot ethanol (14 mL), and water (3.5 mL) was added dropwise while keeping the solution hot. It was left standing overnight at room temperature. The crystals thus prepared (1.73 g) were collected by filtration, washed with 5 mL of a 1:1 ethanol-water mixture and dried under vacuum overnight. The yield was 80% of theory and the melting point was 128°-130° C.

(b) (1R-cis)-1,8-Diethyl-2,3,4,9-tetrahydro-4-(2-propenyl)-1H-carbazole-1-acetic Acid Benzenemethanamine Salt (1:1).

The salt (1R-cis)-1,8-diethyl-2,3,4,9-tetrahydro-4-(2-propenyl)-1H-carbazole-1-acetic acid 2,3-dimethoxy-strychnidin-10-one salt (1:1) (1.73 g) was suspended in 100 mL of ether and treated with 1M hydrochloric acid with stirring. The layers were separated, and the organic layer was washed with a saturated sodium chloride (aq) solution. It was dried over sodium sulfate, filtered and evaporated to a colorless oil (765 mg, 99% yield). This was dissolved in ether (5 mL) and treated with a solution of benzenemethanamine (255 mg) in 2 mL of ether to give a clear solution. Upon standing at room temperature for 2 hours, a crystalline product precipitated and the solution was stored in a refrigerator overnight. The crystals were collected by filtration and washed with a small amount of ether and dried under high vacuum at room temperature to afford 715 mg of the title compound (m.p. 133.5°–134° C., [α]$_D$−93°). The material was 99.9% chirally pure as determined by HPLC of the methyl ester of the free acid on a chiral chromatography column. The absolute and relative configuration were determined by x-ray crystallography.

Elemental Anal. Calcd.: C, 77.74%, H, 8.39%; N, 6.48%. Found: C, 77.58%; H, 8.16%; N, 6.51%.

IR (KBr): 3340 (NH), COOH (broad), 3080–2850 (CH), 1640 (C=O).

NMR (CDCl$_3$, 200 MHz); δ 0.85 (t, 3H, J=7.5), 1.32 (t, 3H, J=7.6), 1.6–2.3 (m, 7H), 2.6 (m, 2H), 2.7 (m, 1H), 2.80 (q, 2H, J=7.6), 3 (m, 1H), 3.86 (s, 2H), 4.3 (broad s), 5–5.2 (m, 2H), 5.8–6 (m, 1H), 6.9–7.1 (m, 2H), 7.2–7.4 (m, 6H), 9.9 (broad s, 1H).

EXAMPLE 45

(1S-cis)-1,8-Diethyl-2,3,4,9-tetrahydro-4-(2-propenyl)-1H-carbazole-1-acetic Acid Benzenemethanamine Salt (1:1)

(a) Preparation of (1S-cis)-1,8-Diethyl-2,3,4,9-tetrahydro-4-(2-propenyl)-1H-carbazole-1-acetic Acid 2,3-Dimethoxy-strychnidin-10-one Salt (1:1)

The mother liquor from the first crystallization of Example 44, step (a), was saturated with water (5 mL) and put in a refrigerator overnight. The crystals were collected by filtration and washed with a 1:1 mixture of ethanol-water (10 mL) to give an enriched mixture of the brucine salt. This material was dissolved in 10 mL of hot ethanol and 1 ml of water was added. The solution was seeded with the product from Example 44, step (a) and left at room temperature overnight. Crystals (385 mg) were filtered and the mother liquor was saturated with water (30 mL). The precipitate that formed (1.5 g) was dissolved in 8 mL of hot ethanol, treated with 3 mL of water and left at room temperature overnight. The crystals were filtered, and 5 mL of water were added to the filtrate. Upon crystallization overnight in the refrigerator, a white crystalline compound (1.1 g) was obtained. Recrystallization twice from hot ethanol (3 mL) and water (1.5 mL) at room temperature afforded the brucine salt (600 mg, 28% yield) 99.9% chirally pure by HPLC done on the methyl ester of the free acid.

(b) (1S-cis)-1,8-Diethyl-2,3,4,9-tetrahydro-4-(2-propenyl)-1H-carbazole-1-acetic Acid Benzenemethanamine Salt (1:1)

The brucine salt from step (a) (600 mg) was suspended in ether and treated with 1M hydrochloric acid. The layers were separated and the organic layer was washed with a saturated sodium chloride (aq) solution. It was dried over sodium sulfate, filtered and evaporated to give a colorless oil (265 mg, 99% yield). This material was dissolved in 1.5 mL of ether and treated with benzenemethanamine (88 mg) in 0.5 mL of ether. Upon standing at room temperature for 2 hours and in the refrigerator overnight, a crystalline product precipitated out of solution. The crystals were collected by filtration and washed with a small amount of ether. They were dried under vacuum at room temperature to afford 248 mg (70% yield, m.p. 133°–134°, [α]$_D$+91.5°, 99.9% chirally pure as determined by HPLC of the methyl ester) of the free acid of the title compound.

Elemental Anal. Calcd.: C, 77.74%; H, 8.39%; N, 6.48%. Found: C, 77.75%; H, 8.29%; N, 6.49%.

IR (KBr): 3340 (NH), COOH (broad), 3080–2850 (CH), 1640 (C=O).

NMR (CDCl$_3$, 200 MHz): δ 0.85 (t, 3H, J=7.5), 1.31 (t, 3H, J=7.6), 1.6–2.3 (m, 7H), 2.5 (m, 2H), 2.65 (m, 1H), 2.8 (q, 2H, J=7.6), 3 (m, 1H), 3.85 (s, 2H), 4.63 (broad s), 5–5.2 (m, 2H), 5.8–6 (m, 1H), 6.9–7.1 (m, 2H), 7.2–7.4 (m, 6H), 10 (broad s, 1H).

EXAMPLE 48

[1α,4α(Z)]-4-(2-Butenyl)-1-ethyl-2,3,4,9-tetrahydro-8-methyl-1H-carbazole-1-acetic Acid (a) Preparation of cis-1-Ethyl-2-oxo-4-(2-oxoethyl)cyclohexaneacetic Acid Methyl Ester A solution of cis-1-ethyl-2-oxo-4-(2-propenyl)cyclohexaneacetic acid methyl ester, prepared by the process of Example 1, step (d) (42.02 mmol, 10 g) in 282 mL of THF and 93 mL of water was stirred mechanically at 0° C. and treated with 214 mg (0.840 mmol, 10.83 mL of 2.5% w/w solution in tert-butanol, d=0.7887) of OsO$_4$. After 15 minutes, the brown reaction mixture was treated with 126.1 mmol (26.96 g) of sodium periodate, the ice bath was removed and the off-white viscous reaction was stirred for 1 hour. It was diluted with 300 mL of brine and extracted with 4×200 mL of ether. Drying (MgSO$_4$) and flash chromatography (95 mm column, 35% EtOAc/petroleum ether eluent) afforded 6.89 g (28.71 mmol, 68%) of dark brown oil.

NMR (CDCl$_3$/TMS, 200 MHz): δ 0.81 (t, 3H, J=7.62), 1.5–2.8 (m, 13H), 3.65 (s, 3H), 9.78 (s, 1H).

IR (neat): 3000–2800 (CH), 2710 (CHO), 1740–1690 (broad C:O).

(b) Preparation of cis-1-Ethyl-4-(2-hydroxyethyl)-2-oxocyclohexaneacetic Acid Methyl Ester Lithium aluminum hydride (200 mmol, 7.59 g) was stirred in 800 mL of tetrahydrofuran at room temperature under nitrogen and treated dropwise with 620 mmol (72.04 g, 87.43 mL) of 3-ethyl-3-pentanol. After completion of the addition, the reaction mixture was refluxed for 1 hour. It was then transferred to a graduated addition funnel where the volume was measured to be 950 mL, thus affording a 0.21M solution of the reducing agent. Of this, 132 mL were added dropwise to a solution of cis-1-ethyl-2-oxo-4-(2-oxoethyl)cyclohexaneacetic acid methyl ester (124 mmol, 29.8 g) in 496 mL of tetrahydrofuran at −78° C. under nitrogen. After 25 minutes, the reaction was quenched gradually with portions of 1M HCl (total volume added=530 mL) as it was warmed to room temperature. The mixture was extracted with 1×400 mL and 2×200 mL of ether and the extracts were combined, dried over magnesium sulfate and concentrated. The remaining 3-ethyl-3-pentanol was removed by distillation under full vacuum (b.p.=room temperature) leaving 27.9 g (115 mmol, 93%) of the primary alcohol (brown oil) in the pot.

$^1$H NMR(CDCl$_3$/TMS, 200 MHz): δ 0.8 (t, 3H, J=7.8 Hz), 1.5–2.5 (m, 11H), 2.5 (d, 1H, J=15 Hz), 2.6 (d, 1H, J=15 Hz), 3.6 (s, 3H), 3.7 (t, 2H, J=6.8 Hz).

IR (thin film): 3410, 2920, 2860, 1720 cm$^{-1}$.

(c) Preparation of cis-4-[2-(Acetyloxy)ethyl]-1-ethyl-2-oxocyclohexaneacetic Acid Methyl Ester A solution of cis-1-ethyl-2-oxo-4-(2-oxoethyl)cyclohexaneacetic acid methyl ester (27.9 g, 115 mmol) in 115 mL of dry methylene chloride was treated with 172 mmol (17.5 g, 24.1 mL) of triethylamine followed by 150 mmol (15.3 g, 14.6 mL) of acetic anhydride and finally a few mg of 4-dimethylaminopyridine. The reaction was stirred for 20 minutes and then diluted with 150 mL of n-pentane and washed with 2×100 mL of 1M HCl and 2×100 mL of saturated NaHCO₃(aq). Drying (MgSO₄) and flash chromatography (95 mm column, 15% ethyl acetate in petroleum ether eluant) afforded 29.7 g (104 mmol, 91%) of yellow oily product. $^1$H NMR(CDCl₃/TMS, 200 MHz); δ 0.8 (t, 3H, J=7.6 Hz), 1.4–2.6 (m, 13H), 2.0 (s, 3H), 3.6 (s, 3H), 4.1 (t, 2H, J=6.5 Hz)

IR (CHCl₃): 3020, 2850, 1730, 1705 cm$^{-1}$.

(d) Preparation of cis-1-Ethyl-2,3,4,9-tetrahydro-8-methyl-4-(2-hydroxyethyl)-1H-carbazole-1-acetic Acid Methyl Ester A solution of cis-4-[2-(acetyloxy)ethyl]-1-ethyl-2-oxocyclohexaneacetic acid methyl ester (129.6 mmol, 36.80 g) and 2-methylphenylhydrazine (38.7 mmol, 5.28 g) in 259 mL of toluene was refluxed for 4 hours under nitrogen with azeotropic removal of water. At this point, TLC analysis demonstrated complete formation of the hydrazone and the reaction was stored in a freezer overnight. The toluene was then removed on a rotovap and replaced with 92 mL of acetic acid. This solution was treated with 168 mmol (23.9 g, 20.7 mL) of boron trifluoride etherate and refluxed under nitrogen for 20 minutes. The reaction mixture was then poured into 800 mL of water and extracted with 4×300 mL of ether. The extracts were combined and washed with 2×350 mL of 1M HCl followed by 2×300 mL of 2.5M NaOH. Drying (MgSO₄) and flash chromatography (95 mm column, 10% ethyl acetate in petroleum ether eluant) afforded 18.32 g, 49.4 mmol, 38%) of a yellow solid. Of this, 10.25 g (27.6 mmol) were stirred under nitrogen in 120 mL of methanol and treated with 764 mg (5.53 mmol) of anhydrous potassium carbonate. After 3 hours, another 250 mg of K₂CO₃ were added and 1.5 hours later, the reaction was quenched with 50 mL of 1M HCl, stripped of solvents and redissolved in ether. It was washed with 100 mL of brine, dried over MgSO₄ and concentrated to afford 9.03 g (27.45 mmol, 99%) a beige solid.

$^1$H NMR(CDCl₃/TMS, 200 MHz): δ 0.84 (t, 3H), 1.2–2.3 (m, 8H), 2.5 (s, 3H), 2.7 (ABq, 2H), 3.2 (m, 1H), 3.7 (s, 3H), 3.84 (t, 2H), 7 (m, 2H), 7.4 (d, 1H), 9.4 (broad s, 1H)

IR (KBr): 3440, 3270, 3050, 2930, 2870, 1700 cm$^{-1}$.

(e) Preparation of cis-1-Ethyl-2,3,4,9-tetrahydro-8-methyl-4-(2-oxoethyl)-1H-carbazole-1-acetic Acid Methyl Ester Two mmol (851 mg) of 1,2-benziodoxol-3(1H)-one, 1,1,1-tris(acetyloxy)-1,1-dihydro were stirred under nitrogen at room temperature in 8 mL of anhydrous acetonitrile and treated portionwise with a solution of cis-1-ethyl-2,3,4,9-tetrahydro-8-methyl-4-(2-hydroxyethyl)-1H-carbazole-1-acetic acid methyl ester (1.82 mmol, 600 mg) in 7.28 mL of acetonitrile. After 5 minutes, the reaction was diluted with 25 mL of ether and washed with 25 mL of 1M sodium hydroxide. The aqueous phase was extracted with 3×15 mL of ether, and the four ether layers were combined, dried over magnesium sulfate and concentrated under vacuum. Flash chromatography (40 mm column, 1% ether-methylene chloride) afforded 367 mg (1.12 mmol, 62%) of a yellow oil.

$^1$H NMR(CDCl₃, 400 MHz): δ 0.85 (t, 3H, J=7.5 Hz), 1.6–2.34 (m, 6H), 2.49 (s, 3H), 2.6–2.74 (m, 2H), 2.94–3.02 (m, 1H), 3.6 (m, 1H), 3.72 (s, 3H), 6.94 (d, 1H, J=7.1 Hz), 6.99 (t, 1H, J=7.4 Hz), 7.31 (d, 1H, J=7.6 Hz), 9.49 (broad s, 1H), 9.86 (m, 1H).

IR (KBr): 3410, 3060, 2970, 2930, 2860, 2820, 2720, 1620 cm$^{-1}$.

Anal. Calcd. for C₂₀H₂₅NO₃: C, 73.37; H, 7.70; N, 4.28. Found: C, 73.45; H, 7.85; N, 4.24.

(f) Preparation of [1α,4α(Z)]-4-(2-Butenyl)-1-ethyl-2,3,4,9-tetrahydro-8-methyl-1H-carbazole-1-acetic Acid Ethyltriphenylphosphonium iodide (6.85 mmol, 2.86 g=2.94 g of 97% pure material) was stirred in 31.8 mL of THF under nitrogen and treated dropwise with 6.4 mmol of potassium bis(trimethylsilyl)amide (6.4 mL of a 1M solution in THF prepared from 1,1,1,3,3,3-hexamethyldisilazane and excess potassium hydride). The bright orange reaction mixture was stirred at room temperature for 10 minutes and was then cooled to −78° C. It was treated dropwise with a solution of 4.89 mmol (1.60 g) of cis-1-ethyl-2,3,4,9-tetrahydro-8-methyl-4-(2-oxoethyl)-1H-carbazole-1-acetic acid methyl ester in 4.9 mL of THF and the reaction mixture was warmed to room temperature over 1 hour. It was diluted with 50 mL of 1:1 ether-petroleum ether, poured into 150 mL of water and extracted with 4×60 mL of 1:1 ether-petroleum ether. The extracts were combined, dried over magnesium sulfate and concentrated under vacuum. Flash chromatography (75 mm column, 10% ethyl acetate in petroleum ether eluant) afforded 1.79 g (5.28 mmol, 108%) of a yellow oil. This was stirred under nitrogen in 16 mL of ethanol and treated with 9.8 mL of 2.5N sodium hydroxide. The reaction was refluxed for 45 minutes and then concentrated under vacuum. The residue was treated with 120 mL of 1N HCl and extracted with 4×50 mL of ether. Drying (MgSO₄) and flash chromatography (50 mm column, 2% H₃PO₄ in methanol treated silica gel, 8% ethyl acetate in petroleum ether eluant) afforded 1.48 g (4.55 mmol, 93% from the aldehyde) of a pale yellow solid which was recrystallized from 85:15 petroleum ether-benzene giving 1.10 g of a white flocculent solid, m.p. 120°–121° C. This was dried under vacuum at 70° C. for 24 hours.

$^1$H NMR (CDCl₃, 400 MHz): δ 0.89 (t, 3H, J=7.5 Hz), 1.65 (d, 3H, J=5.3 Hz), 1.6–2.06 (m, 6H), 2.3 (m, 1H), 2.46 (s, 3H), 2.7 (m, 1H), 2.77 (s, 2H), 3.03 (m, 1H), 5.5 (m, 2H), 6.94 (d, 1H, J=7.1 Hz), 6.99 (t, 1H, J=7.4 Hz), 7.45 (d, 1H, J=7.7 Hz), 8.89 (broad s, 1H).

$^{13}$C NMR (CDCl₃, 100.6 MHz): δ 8.75, 13.06, 16.52, 24.18, 30.13, 30.82, 31.96, 32.53, 36.93, 43.25, 114.12, 116.81, 119.13, 119.97, 121.82, 124.98, 126.00, 129.28, 135.27, 138.53, 179.00.

IR (KBr): 3420, 3050, 3010, 2960, 2930, 2870, 1705, 1685 cm$^{-1}$.

Anal. Calcd. for C₂₁H₂₇NO₂: C, 77.50; H, 8.36; N, 4.30. Found: C, 77.34; H, 8.12; N, 4.33.

The compound of Example 1, cis-1,8-diethyl-2,3,4,9-tetrahydro-4-(2-propenyl)-1H-carbazole-1-acetic acid, can also be prepared by the process of this example by substituting 2-ethylphenylhydrazine for 2-methylphenylhydrazine in step (d) and by substituting methyltriphenylphosphonium iodide for ethyltriphenylphosphonium iodide in step (f).

EXAMPLE 49 cis-1-Ethyl-7,8-difluoro-2,3,4,9-tetrahydro-4-(2-propenyl)-1H-carbazole-1-acetic Acid (a) Preparation of 2,3-Difluorophenylhydrazine In each of two flasks, 775 mmol (100 g) of 2,3-difluoroaniline were added to 2 L of concentrated hydrochloric acid at −15° C. and treated dropwise with a solution of 852 mmol (58.9 g) of sodium nitrite in 500 mL of water. Ten minutes after the addition, the reaction was treated with 930 mmol (55.8 g) of urea. This was followed by rapid addition of a solution of stannous chloride dihydrate (968 mmol, 220 g) in 700 mL of concentrated hydrochloric acid precooled to −50° C. After 20 minutes, the solid from both reactions was filtered and combined. It was put into 3 L of 1M NaOH (aq) and extracted with 4×500 mL of ether. The extracts were combined, dried over MgSO$_4$ and concentrated to afford 110 g of 2,3-difluorophenylhydrazine (763 mmol, 49%).

NMR (CDCl$_3$/TMS, 200 MHz): 3.59 (broad s, 2H), 5.49 (broad s, 1H), 6.5–6.6 (m, 1H), 6.8–7 (m, 2H).

(b) Preparation of cis-1-Ethyl-7,8-difluoro-2,3,4,9-tetrahydro-4-(2-propenyl)-1H-carbazole-1-acetic Acid A solution of cis-1-ethyl-2-oxo-4-(2-propenyl)cyclohexaneacetic acid methyl ester, prepared by the process of Example 1, step (d) (24.5 mmol, 5.8 g) and 2,3-difluorophenylhydrazine (27.0 mmol, 3.9 g) was refluxed in 50 mL of toluene for 8 days with azeotropic removal of water. The toluene was then removed under reduced pressure and replaced with 30 mL of acetic acid. The solution was then treated with 29.4 mmol (4.17 g, 3.6 mL) of boron trifluoride etherate and refluxed for 20 minutes under nitrogen. The reaction mixture was then poured into 100 mL of water and extracted four times with ether. The ether extracts were combined, washed with 1M HCl (aq) and twice with 1M NaOH (aq). Drying (MgSO$_4$) and flash chromatography (50 mm column, 5% EtOAc/petroleum ether eluant) afforded 3.5 g (10.1 mmol, 41%) of a yellow oil. This was then refluxed in a solution of 8 mL of 2.5N NaOH (aq) and 24 mL of ethanol for 30 minutes under nitrogen. The ethanol was removed under reduced pressure and the residue was dissolved in 1M HCL. It was extracted with ether and dried over MgSO$_4$. Flash chromatography (50 mm column, 20% ethyl acetate in petroleum ether eluant, 2% H$_3$PO$_4$ in MeOH treated silica gel) afforded 3.2 g (9.60 mmol, 95%) as a yellow oil which was triturated with n-pentane. This gave 1.8 g of a white powder, m.p. 105°–107° C., which was dried under vacuum at 80° C. over silica.

Anal. Calcd.: C, 68.45; H, 6.35; N, 4.20. Found: C, 68.10; H, 6.21; N, 4.59.

IR (KBr): 3440, 3080, 2980, 2930, 2905, 2850, 2820, 1710, 1650, 1600.

NMR (CDCl$_3$, 400 MHz): δ 0.88 (t, 3H, J=7.5), 1.68–2.04 (m, 6H), 2.24–2.33 (m, 1H), 2.6–2.68 (m, 1H), 2.75 (s, 2H), 2.98–3.04 (m, 1H), 5–5.1 (m, 2H), 5.78–5.88 (m, 1H), 6.82–6.9 (m, 1H), 7.15–7.2 (m, 1H), 9.16 (s, 1H).

We claim:

1. The compounds designated 1-ethyl-7,8-difluoro-2,3,4,9-tetrahydro-4-(2-propenyl)-1H-carbazole-1-acetic acid and the pharmaceutically acceptable salts thereof.

2. The compound according to claim 1 designated cis-1-ethyl-7,8-difluoro-2,3,4,9-tetrahydro-4-(2-propenyl)-1H-carbazole-1-acetic acid and the pharmaceutically acceptable salts thereof.

3. The compound designated 1-ethyl-2,3,4,9-tetrahydro-4-(phenylmethyl)-1H-carbazole-1-acetic acid and the pharmaceutically acceptable salt thereof.

4. The compound designated 7-chloro-1-ethyl-2,3,4,9-tetrahydro-8-methyl-4-(phenylmethyl)-1H-carbazole-1-acetic acid and the pharmaceutically acceptable salt thereof.

* * * * *